(12) United States Patent
Boldingh (10) Patent No.: US 6,191,331 B1
(45) Date of Patent: Feb. 20, 2001

(54) ZEOLITE CATALYST PRECOKING METHOD FOR SELECTIVE AROMATICS DISPROPORTIONATION PROCESS

(75) Inventor: Edwin P. Boldingh, Arlington Heights, IL (US)

(73) Assignee: UOP LLC, Des Plaines, IL (US)

( * ) Notice: Under 35 U.S.C. 154(b), the term of this patent shall be extended for 0 days.

(21) Appl. No.: 09/347,805

(22) Filed: Jul. 2, 1999

(51) Int. Cl.$^7$ ................ C07C 5/22; C07C 5/52; C07C 15/12
(52) U.S. Cl. ............................ 585/475; 585/470
(58) Field of Search ........................ 585/70, 75

(56) References Cited

U.S. PATENT DOCUMENTS

| | | | |
|---|---|---|---|
| 4,097,543 | 6/1978 | Haag et al. | 260/672 T |
| 4,537,866 | * 8/1985 | Gilson | 502/70 |
| 4,629,717 | * 12/1986 | Chao | 502/208 |
| 5,495,061 | * 2/1996 | Kulprathipanja | 585/828 |
| 5,866,740 | * 8/1985 | Mikitenko et al. | 585/470 |

* cited by examiner

Primary Examiner—Marian C. Knode
Assistant Examiner—Thuan D. Dang
(74) Attorney, Agent, or Firm—John G. Tolomei; John F. Spears, Jr.; Thomas K. McBride, Jr.

(57) ABSTRACT

An improved process is disclosed for the selective disproportionation of toluene. The process uses a zeolitic catalyst which is selectively precoked prior to toluene disproportionation in a manner to avoid a large temperature rise across a bed of the catalyst during precoking. The catalyst and process provide enhanced selectivity for the production of paraxylene.

19 Claims, 6 Drawing Sheets

ZEOLITE CATALYST PRECOKING METHOD FOR SELECTIVE AROMATICS DISPROPORTIONATION PROCESS

BACKGROUND OF THE INVENTION

This invention relates to an improved process for the conversion of aromatic hydrocarbons. More specifically, the invention concerns disproportionation and transalkylation of aromatic hydrocarbons to obtain xylenes.

The xylene isomers are produced in large volumes from petroleum as feedstocks for a variety of important industrial chemicals. The most important of the xylene isomers is paraxylene, the principal feedstock for polyester which continues to enjoy a high growth rate from large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics along with toluene have been commercialized to obtain high xylene yields.

U.S. Pat. No. 4,097,543 (Haag et al.) teaches toluene disproportionation for the selective production of paraxylene using a zeolite which has undergone controlled precoking. The zeolite may be ion-exchanged with a variety of elements from Group IB to VIII, and composited with a variety of clays and other porous matrix materials.

Workers in the field of aromatics disproportionation continue to seek processes and catalysts having exceptionally high selectivity for paraxylene from toluene combined with favorable activity and stability.

SUMMARY OF THE INVENTION

It is an object of the present invention to provide an improved process for the disproportionation of aromatic hydrocarbons to yield desirable alkylaromatic isomers. A specific objective is to obtain a high yield of paraxylene by disproportionation of toluene.

This invention is based on the discovery that high activity with potential for selectivity to paraxylene is obtained by disproportionation of toluene using a zeolitic catalyst which has been selectively precoked with no more than a small temperature rise across a bed of the zeolitic catalyst during precoking.

The present invention therefore is directed to process steps for paraxylene-production comprising the selective precoking of a zeolitic catalyst, with a temperature differential of less than about a 3° C. increase across a bed of the zeolitic catalyst, and disproportionation of a toluene feedstock using the precoked catalyst to obtain a paraxylene-rich product comprising paraxylene in excess of its equilibrium concentration at disproportionation conditions. Preferably the temperature differential across the zeolitic catalyst bed during selective precoking is between about a 3° C. increase and a 10° C. decrease, and more preferably between about a 2° C. increase and a 5° C. decrease.

The catalyst preferably comprises a zeolitic aluminosilicate having a pore diameter of from about 5 to 8 Å, most preferably MFI, and an amorphous aluminum phosphate binder. In one embodiment, the catalyst has a particle size of no more than about 1 mm.

A process combination optionally comprises a xylene-separation zone; preferably, paraxylene is recovered by adsorption.

These as well as other objects and embodiments will become apparent from the detailed description of the invention.

DESCRIPTION OF THE PREFERRED EMBODIMENTS

An embodiment of the present invention therefore is directed to process steps for the disproportionation of a toluene feedstock to obtain a product comprising paraxylene using a zeolitic catalyst which has been subjected to a precoking step with less than about a 3° C. temperature increase across a bed of the zeolitic catalyst, prior to its use for disproportionation, in order to deposit a controlled concentration of carbon on the catalyst and increase paraxylene selectivity in the disproportionation step. The paraxylene content of the paraxylene-rich product from disproportionation is in excess of its equilibrium concentration at disproportionation conditions. Other embodiments of the invention encompass but are not limited to parameters such as incremental and alternative feedstocks, catalyst composition, catalyst conditioning for paraxylene selectivity and operating conditions.

The zeolitic catalyst is subjected to selective precoking to increase the proportion of paraxylene in the paraxylene-rich product above equilibrium levels at disproportionation conditions. Precoking of the present catalyst effects a proportion of paraxylene in the product above equilibrium levels at disproportionation conditions, preferably at least about 80 mass-% and optimally about 90 mass-% or more of the $C_8$ aromatics. Precoking is effected on a fresh or regenerated catalyst, prior to its use for disproportionation, for a time ranging from about 0.5 hours to 10 days.

Critical precoking conditions according to the present invention control the temperature differential across a bed of the catalyst during the precoking step. It has been found that an excessive increase in temperature from the inlet to the exit of the catalyst bed has a strong adverse effect on the selectivity to paraxylene in the subsequent disproportionation step. Precoking is effected with a temperature differential of less than about a 3° C. increase across a bed of the zeolitic catalyst, that is, the temperature of reactants leaving the catalyst bed during precoking is less than 3° C. higher than the temperature of the feedstock entering the catalyst bed. Preferably the temperature differential across the zeolitic catalyst bed during selective precoking is between about a 2° C. increase and a 4° C. decrease, and more preferably less than about at 1° C. increase.

The temperature differential as defined above and in the claims applies to the overall average, which also may be characterized as an intermediate value, during the precoking/selectivation step. The control of the temperature differential during the initial precoking phase (generally about the first 10% of the duration) of the selectivation is the most critical to subsequent disproportionation results, however, since generally more than 50% and more typically 70% or more of the coke is deposited during this initial precoking phase. Consequently, the indicated restrictions on precoking temperature differential apply optimally during the initial precoking phase.

The critically effective precoking is effected at conditions relative to the subsequent disproportionation step comprising one or more of a higher temperature, lower pressure, lower space velocity, and lower hydrogen-to-hydrocarbon ratio. Such precoking conditions comprise a pressure of from about 100 kPa to 4 MPa absolute, and a liquid hourly space velocity of from about 0.2 to 10 $hr^{-1}$ The critical conditions comprise one or more of an inlet temperature at least about 50° C. higher; a pressure at least about 100 kPa lower, or preferably no more than about half of the pressure utilized in the subsequent disproportionation step. Preferably the molar ratio of free hydrogen to feedstock hydrocarbons is no more than about half of that utilized in the subsequent disproportionation zone. Lower pressure and/or a lower hydrogen/hydrocarbon ratio will lower the proportion of exothermic aromatic-saturation reactions, and thus restrict the temperature rise; the result thus should be a relatively flatter temperature profile.

It is believed, without so limiting the invention, that the temperature profile affects the coking rate in various parts of the catalyst bed. A steep temperature gradient therefore will effect non-uniform coke deposition, and different parts of the catalyst bed thus will be selectivated to a different extent causing poorer performance in the subsequent disproportionation step.

Precoking effects a catalyst coke or carbon content of between about 5 and 40 mass-% carbon, and preferably between about 10 and 30 mass-% carbon. A coke-forming feed for precoking may comprise the feedstock to the disproportionation step as described hereinbelow, such as toluene, or other specific hydrocarbons or mixtures known in the art preferably comprising aromatics may be used. Further details relative to precoking are disclosed in U.S. Pat. No. 4,097,543, incorporated herein by reference.

Broadly, an aromatics-rich feedstock to the disproportionation step comprises substantially pure aromatic hydrocarbons derived from one or more sources. Aromatics may be produced synthetically, for example, from naphtha by catalytic reforming or by pyrolysis followed by hydrotreating to yield an aromatics-rich product. The aromatics feedstock may be derived from such product with suitable purity by extraction of aromatic hydrocarbons from a mixture of aromatic and nonaromatic hydrocarbons and fractionation of the extract. Large quantities of aromatic hydrocarbons are recovered commercially in this manner. For instance, aromatics may be recovered from a reformate through the use of a selective solvent, such as one of the sulfolane type, in a liquid-liquid extraction zone. When the severity of reforming or pyrolysis is sufficiently high, extraction may be unnecessary and fractionation may be sufficient to prepare the feedstock which should contain no more than about 10 mass-% and preferably less than about 1 mass-% nonaromatics. The recovered aromatics may then be separated into streams having the desired carbon number range by fractionation. The aromatic hydrocarbons may comprise one or more of toluene, xylene isomers, ethylbenzene, or $C_9$ and heavier aromatics. A preferred toluene feedstock prepared in this manner usually is fractionated to separate benzene and $C_8$ aromatics, and the degree of fractionation may be adjusted in accordance with economic factors of the disproportionation process.

The toluene feedstock, usually in admixture with toluene recycled from the products of the disproportionation reaction, is preferably admixed with free hydrogen to effect a combined feed to a disproportionation zone. If present, the hydrogen need not exceed a 20:1 mole ratio to feedstock hydrocarbons to effect satisfactory stability in the disproportionation reaction, and preferably is in the range of from about 0.5 to 10 mole ratio. The hydrogen may contain hydrocarbons, such as methane and ethane, and inerts such as nitrogen, but preferably is in a concentration of at least about 90 mole-% to avoid large hydrogen losses and unfavorable process economics. The disproportionation reaction yields a paraxylene-rich product which usually also comprises benzene, other $C_8$ aromatics, and smaller amounts of $C_9+$ aromatics.

The combined feed to the disproportionation zone usually is first heated by indirect heat exchange against the effluent of the reaction zone and is then further heated in a fired heater. The vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both the feed and product hydrocarbons. This effluent is normally cooled by indirect heat exchange against the stream entering the reaction zone and then further cooled through the use of air or cooling water. The temperature of the effluent stream is normally lowered sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all $C_5$ and lighter hydrocarbons present in the effluent are concentrated into an overhead stream and removed from the process. An aromatics-rich stream is recovered as net stripper bottoms which is referred to herein as the disproportionation effluent stream.

Conditions employed in the disproportionation zone of the subject process normally include an inlet temperature of from about 200° to about 600° C., and preferably from about 350° to 575° C. The temperature required to maintain the desired degree of conversion will increase as the catalyst gradually loses activity during processing. Normal end-of-run inlet temperatures may therefore exceed start-of-run inlet temperatures by 65° C. or more. In the transalkylation embodiment wherein toluene and $C_9$ aromatics are present in the combined feed, reaction temperatures generally are somewhat lower within the range of about 200° to 525° C.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of paraxylene at the expense of conversion. Liquid hourly space velocities generally are the range of from about 0.2 to 10 $hr^{-1}$, with a value in the range of from 0.8 to 3 $hr^{-1}$ being preferred.

It is within the scope of the invention that the combined feed comprises a heavy-aromatics stream comprising $C_9$ aromatics as a component of the combined feed to the present process. Transalkylation of toluene and $C_9$ aromatics is effected thereby within the disproportionation conditions described hereinabove The heavy-aromatics stream may be derived from the same or different known refinery and petrochemical processes as the toluene feedstock and/or may be recycled from the separation of the product from disproportionation/transalkylation. Benzene also may be present in the combined feed to disproportionation/transalkylation. However, it is preferred that the feedstock consists essentially of toluene in order to effect a high degree of paraxylene selectivity as described herein.

The paraxylene-rich product from the disproportionation step is separated into a light recycle stream, a paraxylene-rich mixed-$C_8$-aromatics product and a heavy-aromatics stream. The paraxylene-rich product may be sent to a xylene-separation zone for recovery of pure paraxylene; optionally, other xylenes and ethylbenzene also may be recovered as pure products. The paraxylene-rich product preferably contains paraxylene in proportion to total xylenes in excess of its equilibrium concentration at disproportionation conditions, more preferably at least about 80 mass-% paraxylene, and most preferably at least about 85 mass-% paraxylene. The light recycle stream may be diverted to other uses such as to benzene and toluene recovery, but preferably is partially recycled to the disproportionation zone since it contains not only benzene and toluene but also amounts of nonaromatics which would remain with the benzene and reduce its commercial value. The heavy recycle stream contains substantially all of the $C_9$ and heavier aromatics and may be either withdrawn as a product of the process or partially or totally recycled to the reaction if transalkylation is an objective of the process.

The xylene-separation zone may utilize one or more different separation techniques such as fractionation, crystallization or selective adsorption to recover pure paraxylene from the paraxylene-rich stream in the xylene-separation zone. Conventional crystallization is disclosed in U.S. Pat. No. 3,177,255, U.S. Pat. No. 3,467,724 and U.S. Pat. No. 3,662,013. Various other crystallization alternatives are discussed in U.S. Pat. No. 5,329,061, incorporated by reference. In an embodiment in which the paraxylene-rich product has a paraxylene content substantially in excess of the equilibrium concentration, recovery of pure paraxylene may be effected using only a single stage of crystallization corresponding to the higher-temperature purification stage of conventional crystallization.

An alternative separation zone comprises a bed of molecular sieves operated in accordance with the teaching of U.S. Pat. No. 3,201,491 to simulate the use of a continuously moving bed of molecular sieves. Subsequent improvements to the process are described in U.S. Pat. No. 3,696,107 and U.S. Pat. No. 3,626,020. Details on the operation of the xylene-separation zone may also be obtained from U.S. Pat. No. 4,039,599 and U.S. Pat. No. 4,184,943. The simulated cocurrent adsorptive separation process of U.S. Pat. No. 4,402,832 may be employed. The extract and raffinate streams may be handled as described in these references or as described in U.S. Pat. No. 4,381,419.

The skilled routineer will recognize variations in the process combination described above which are within the scope of the invention. For example, benzene as well as toluene may be charged to the disproportionation zone as a supplementary feedstock. The xylene-separation zone may use one or more of several known separation techniques such as adsorption, crystallization and fractionation. Orthoxylene and/or metaxylene may be recovered as pure products from the xylene-separation zone.

The catalyst of the present invention comprises a molecular sieve and a refractory inorganic oxide. The preferred molecular sieves are zeolites, or zeolitic aluminosilicates, having a Si:$Al_2$ ratio greater than about 10, preferably greater than 20, and a pore diameter of about 5 to 8 Angstroms (Å). Specific examples of preferred zeolites are the MFI, MEL, EUO, FER, MFS, MTT, MTW, TON, MOR and FAU types. Pentasil zeolites MFI, MEL, MTW and TON are favored, and MFI-type zeolites, often designated ZSM-5, are especially preferred.

The preparation of the preferred MFI-type zeolites is well known in the art. The zeolites generally are prepared by crystallizing a mixture containing an alumina source, a silica source, an alkali metal source, water and an alkyl ammonium compound or its precursor. The amount of zeolite present in the catalyst can vary considerably but usually is present in an amount from about 30 to 90 mass percent and preferably from about 50 to 80 mass percent of the catalyst.

A refractory binder or matrix is utilized to facilitate fabrication of the disproportionation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, zinc oxide and silica. Alumina and/or silica are preferred binders.

A preferred binder or matrix component is a phosphorus-containing alumina (hereinafter referred to as aluminum phosphate) component. The phosphorus may be incorporated with the alumina in any acceptable manner known in the art. The zeolite and aluminum phosphate binder are mixed and formed into particles by means well known in the art such as gellation, pilling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/zeolite/phosphorus compound into particles by employing the oil-drop method described hereinbelow, and calcining the spherical particles.

The preferred oil-drop method of preparing the aluminum phosphate is described in U.S. Pat. No. 4,629,717 which is incorporated by reference. The technique described in the '717 patent involves the gellation of a hydrosol of alumina which contains a phosphorus compound using the well-known oil-drop method. The amount of phosphorus-containing alumina component present (as the oxide) in the catalyst can range from about 10 to 70 mass percent and preferably from about 20 to 50 mass percent.

The combined mixture preferably is dispersed into the oil bath in the form of droplets from a nozzle, orifice or rotating disk. Alternatively, the particles may be formed by spray-drying of the mixture at a temperature of from about 425° to 760° C. In any event, conditions and equipment should be selected to obtain small spherical particles; the particles preferably should have an average diameter of less than about 1.0 mm, more preferably from about 0.2 to 0.8 mm, and optimally from about 0.3 to 0.8 mm.

The aluminum-phosphate binder generally is amorphous, i.e., the binder material is essentially of amorphous character, with preferably less than about 10 mass-% of the binder pore volume as micropore volume. The aluminum phosphate binder/matrix also may contain lesser proportions of other inorganic oxides including, but not limited to, magnesia, beryllia, boria, silica, germania, tin oxide, zinc oxide, titania, zirconia, vanadia, iron oxide, chromia, cobalt oxide and the like which can be added to the hydrosol prior to dropping.

It is within the scope of the invention that the catalyst contains a metal component, preferably selected from components of the group consisting of gallium, rhenium and bismuth. Preferably, however, the catalyst consists essentially of a zeolitic aluminosilicate having a pore diameter of from about 5 to 8 Å and an amorphous aluminum phosphate binder.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

An aluminum-phosphate-bound MFI catalyst was prepared to compare the process of the invention to the known art. A first solution was prepared by adding phosphoric acid to an aqueous solution of hexamethylenetetraamine (HMT) in an amount to yield a phosphorus content of the finished catalyst equal to about 3.8 mass-% and a alumina: phosphorus atomic ratio in the binder of about 2:1. A second solution was prepared by adding an ammonium-exchanged MFI-type zeolite having an $Si/Al_2$ ratio of about 39 to enough alumina sol, prepared by digesting metallic aluminum in hydrochloric acid, to yield a zeolite content in the finished catalyst equal to about 70 mass-%. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 650° C. This disproportionation catalyst was utilized in the precoking and disproportionation tests described hereinafter.

Example II

Two pilot-plant tests were performed to compare disproportionation results when precoking the catalyst of Example I with an even temperature across a catalyst bed (Test A) in accordance with the invention.

Figure 1:
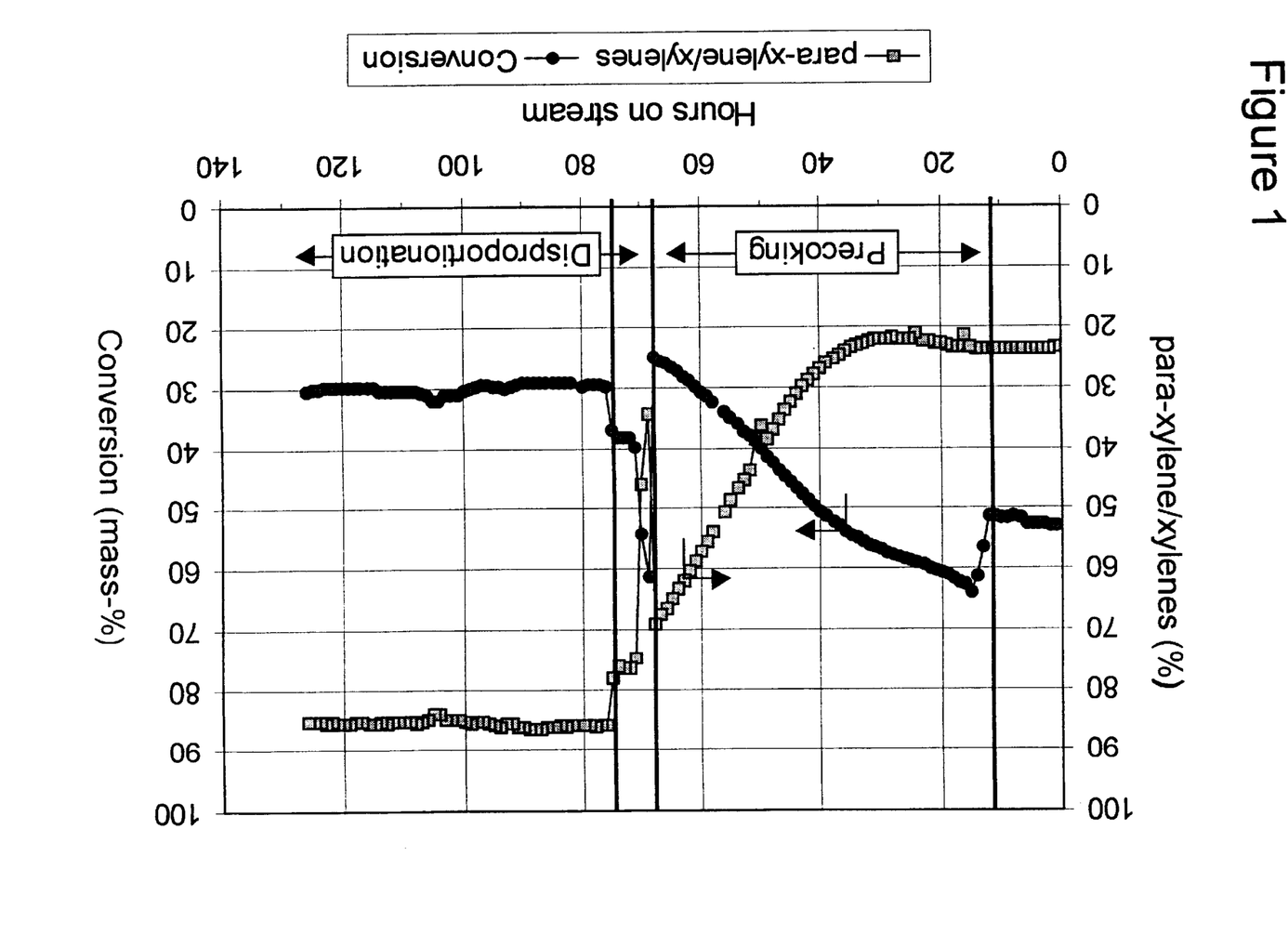
FIG. 1 shows conversion and selectivity in a pilot-plant test of precoking and toluene disproportionation.

The Test A sequence of precoking and disproportionation is shown in FIG. 1. Following a startup period the catalyst was precoked over a period of 57 hours to provide a carbon content sufficient to enhance selectivity. The precoking was effected at 2.86 Mpa, 561° C. and 4 weight hourly space velocity (WHSV) in the presence of nitrogen and at a 0.5:1 hydrogen:hydrocarbon mole ratio. Following a short transition, disproportionation of pure toluene then was carried out over a period of 51 hours at 2.86 Mpa and 4 WHSV in the presence of pure hydrogen at temperatures of 427°–429° C.

An even precoking temperature (0° C. between inlet and outlet)) was maintained during Test A by direct temperature control of the reactor, with the temperature varying no more than a few tenths of a degree over the length of the reactor during each phase of the selectivation. Subsequent disproportionation achieved a benzene/xylene molar ratio of 1.4 at 88.5% paraxylene/xylenes and 30% toluene conversion; of course, 88.5% is well in excess of the equilibrium concentration of 23–24%.

Example III

Tests B and B' utilized a sequence not according to the invention of precoking and disproportionation. In each test, following a startup period, the catalyst was precoked at 2.86 Mpa and 4 weight hourly space velocity (WHSV) in the presence of nitrogen and at a 0.5:1 hydrogen:hydrocarbon mole ratio, over a period of 49 hours, 562° C. for Test B and over a period of 51 hours at 561° C. for Test B'. Disproportionation of pure toluene then was carried out at 2.86 Mpa and 4 WHSV in the presence of pure hydrogen, over a period of 79 hours at variable temperatures of 431°–435° C. for Test B and 42 hours at variable temperatures of 429°–432° C. for Test B'.

Figure 2:
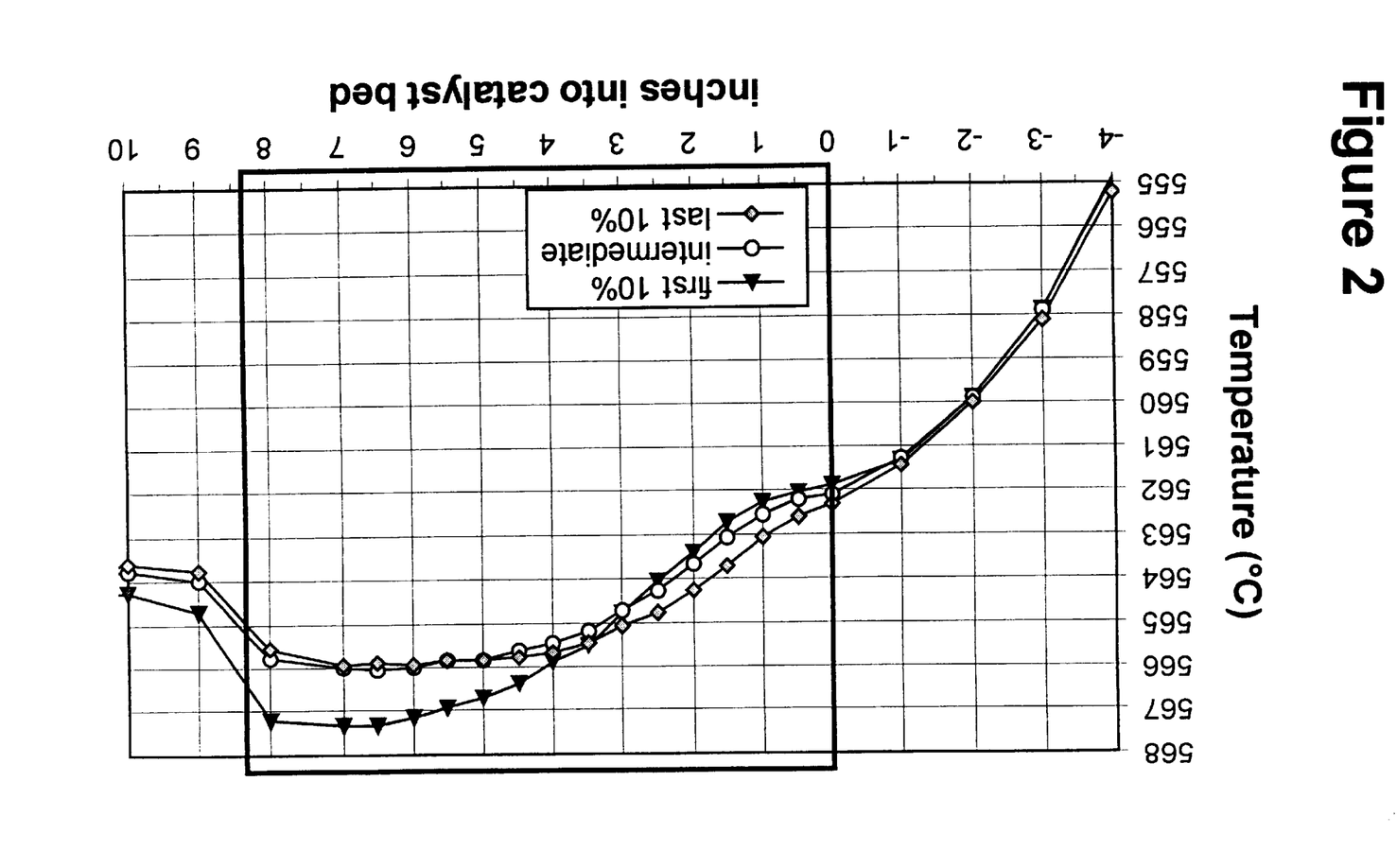
FIG. 2 shows the temperature profile across a catalyst bed during a precoking test with a substantial exotherm.

The temperature profile during the precoking step is shown in FIG. 2 for various stages of the selectivation phase of Test B, averaging hourly readings to obtain the indicated points. The profile results in an average/intermediate increase across the reactor of about 3° C. for Test B, and similar results work out to an average increase of about 4° C. for Test B' (no detailed temperature profile). Subsequent disproportionation showed a benzene/xylene molar ratio of 1.52 at 87.9% paraxylene/xylenes for Test B and 1.56 at 89.1 paraxylene/xylenes for Test B'.

Example IV

A Test C sequence of precoking and disproportionation generally followed the Test A sequence, adjusting the associated furnace to control the temperature differential across the catalyst. Following a startup period the catalyst was precoked over a period of 59 hours to provide a carbon content sufficient to control activity and selectivity. The precoking was effected at 2.86 Mpa, 562° C. and 4 weight hourly space velocity (WHSV) in the presence of nitrogen and at a 0.5:1 hydrogen:hydrocarbon mole ratio. Following transition, disproportionation of pure toluene then was carried out over a period of 63 hours at 2.86 Mpa and 4 WHSV in the presence of pure hydrogen at variable temperatures of 422°–429° C.

Figure 3:
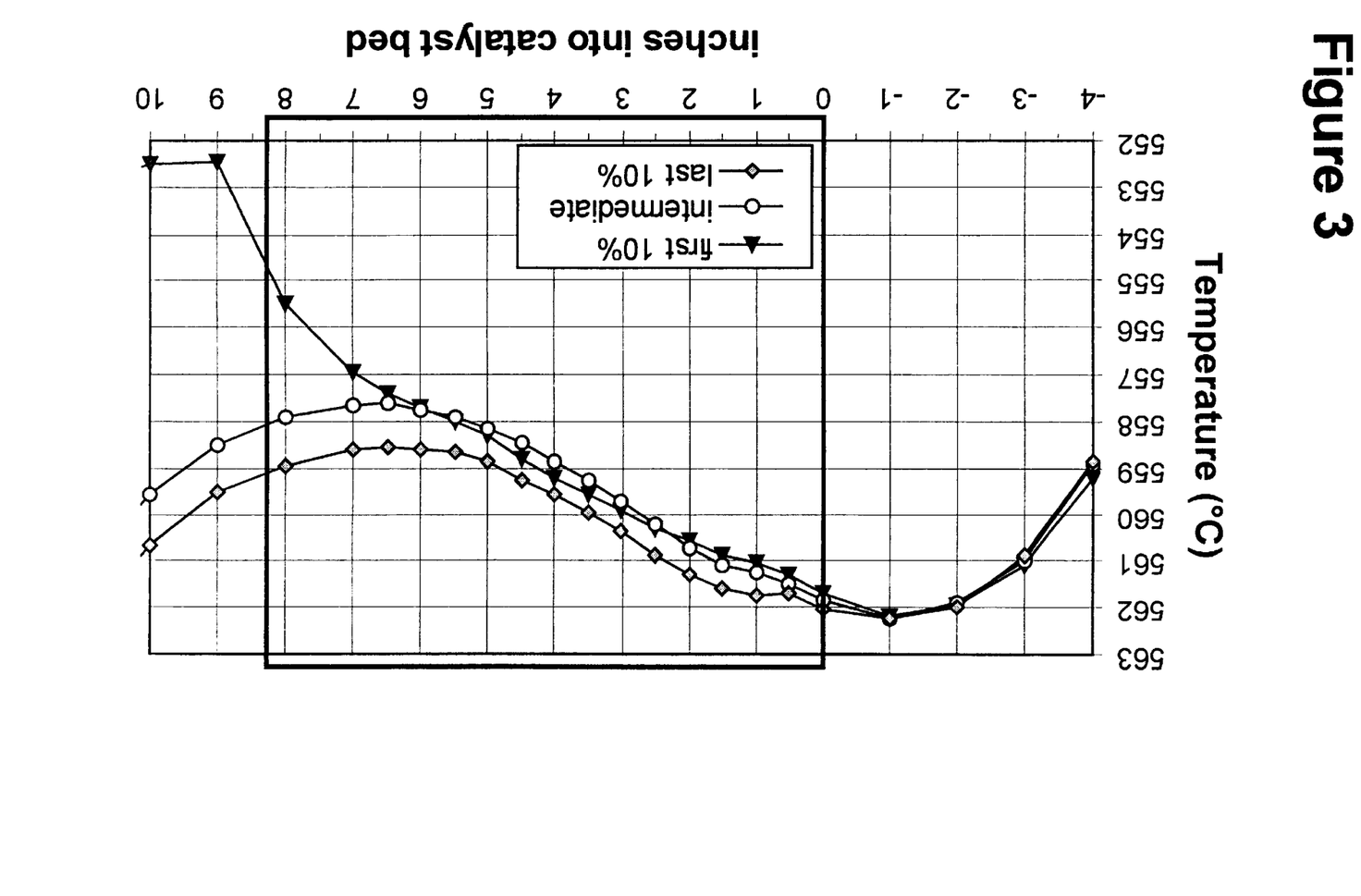
FIG. 3 shows the temperature profile across a catalyst bed during a precoking test with a substantial endotherm.

The temperature profile during the precoking step is shown in FIG. 3 for various stages of the selectivation phase of Test C. The profile shows a significant decline across the reactor at each phase, with an average decline of about 4° C. Subsequent disproportionation showed a benzene/xylene molar ratio of 1.5 at 90.9% paraxylene/xylenes and 30% toluene conversion.

Example V

A pilot-plant Test D was performed to compare disproportionation results when precoking the catalyst of Example I according to the invention at a low pressure relative to the subsequent disproportionation in comparison to precoking not according to the invention described previously(Tests B and B').

Test D included a sequence of precoking and disproportionation, following a startup period, in which the catalyst was precoked over a period of 135 hours to provide a carbon content sufficient to control activity and selectivity. The precoking was effected at a reduced pressure, compared to that of the subsequent disproportionation, of 0.72 Mpa vs. 2.86 Mpa; other precoking conditions comprised a temperature of 561° C. and 4 weight hourly space velocity (WHSV) in the presence of nitrogen and at a 0.5:1 hydrogen:hydrocarbon mole ratio. Disproportionation of pure toluene then was carried out over a period of 95 hours at 2.86 Mpa and 4 WHSV in the presence of pure hydrogen at variable temperatures of 419°–429° C.

Figure 4:
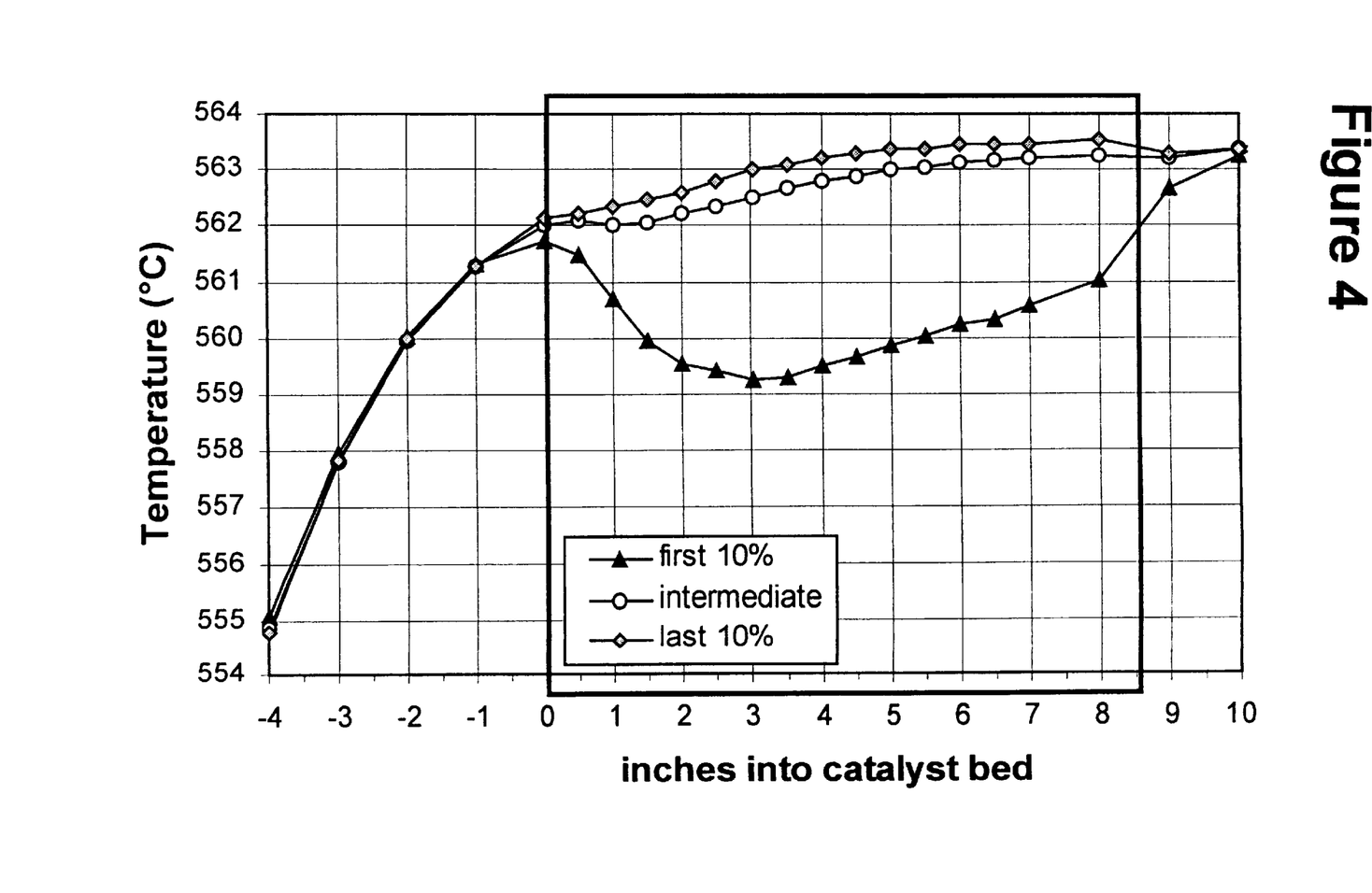
FIG. 4 shows the temperature profile across a catalyst bed during a precoking test according to the invention.

An even temperature (1° C. average increase between inlet and outlet) was maintained during Test D through using a substantially lower pressure for the precoking. The temperature profile through the reactor is shown in FIG. 4. The temperature actually declined through the reactor during the selectivation phase, and then changed to a slight increase (exotherm). The disproportionation achieved a benzene/xylene molar ratio of 1.38 at 88.2% paraxylene/xylenes.

Example VI

Test E included a sequence of precoking and disproportionation, following a startup period, in which the catalyst was precoked according to the art over a period of 190 hours at 2.86 Mpa, 562° C. and 4 weight hourly space velocity (WHSV) in the presence of nitrogen and at a relatively high 1.5:1 hydrogen:hydrocarbon mole ratio. Disproportionation of pure toluene then was carried out over a period of 79 hours at 2.86 Mpa and 4 WHSV in the presence of pure hydrogen at variable temperatures of 458°–486° C.

The temperature profile during the precoking step showed an average increase across the reactor of over 30° C. Subsequent disproportionation showed a benzene/xylene molar ratio of 1.95 at 86% paraxylene/xylenes for Test E.

Example VII

Figure 5:
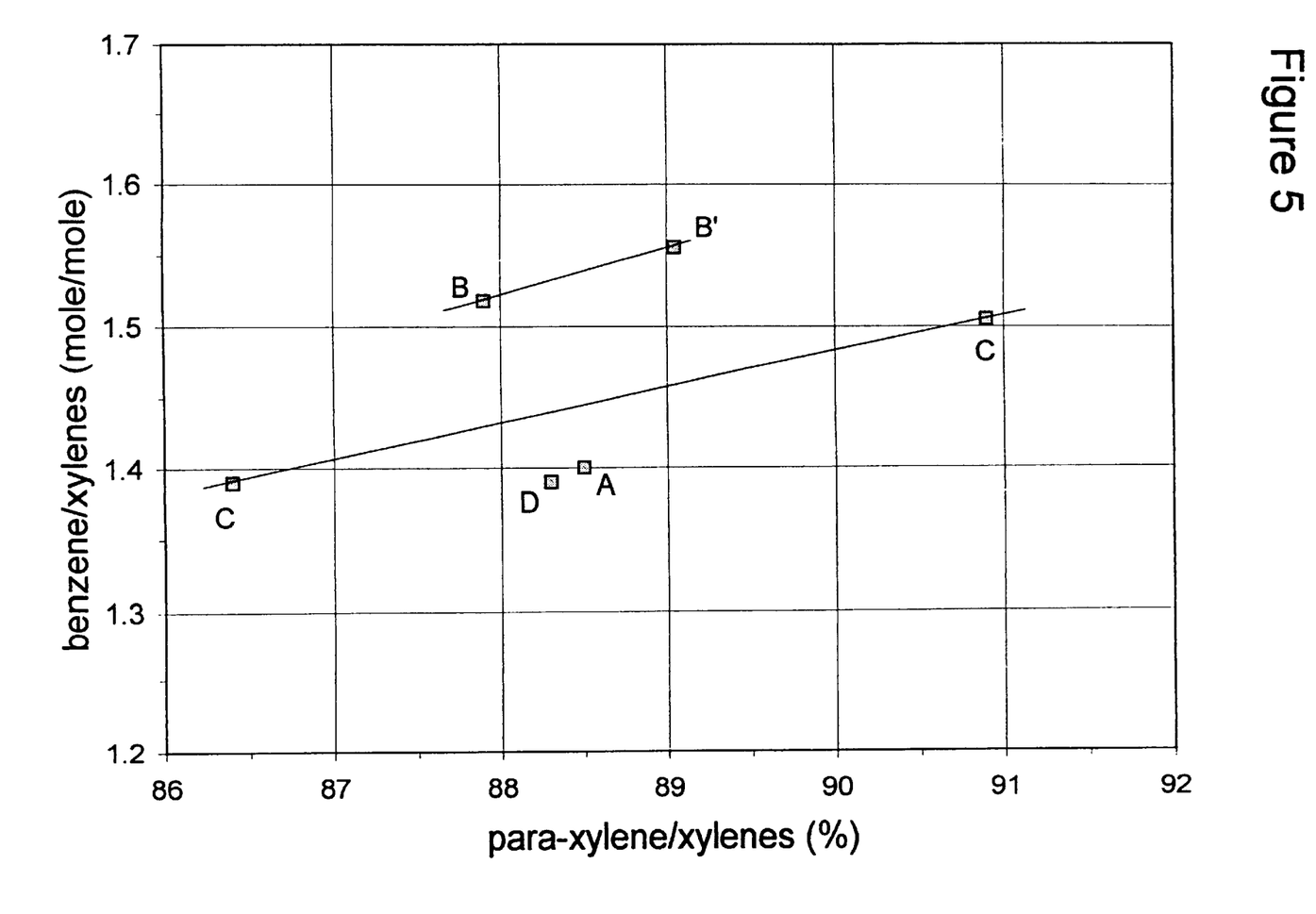
FIG. 5 compares selectivity of various tests as benzene/xylenes ratio as a function of the ratio of paraxylene/xylenes.

A plot of disproportionation results as the ratio of benzene/total xylenes produced vs. the ratio of paraxylene/total xylenes indicates catalyst selectivity. Benzene produced above the stoichiometric 1:1 ratio represents loss of xylenes through saturation and cracking of the aromatic ring. FIG. 5 is a plot of these parameters at 30% toluene (liquid-based) conversion for the tests described in the above examples. Test E of the known art was so unfavorable as to be off the chart. Tests A and D, representing the best examples of the process of the invention, showed a clear advantage.

Figure 6:
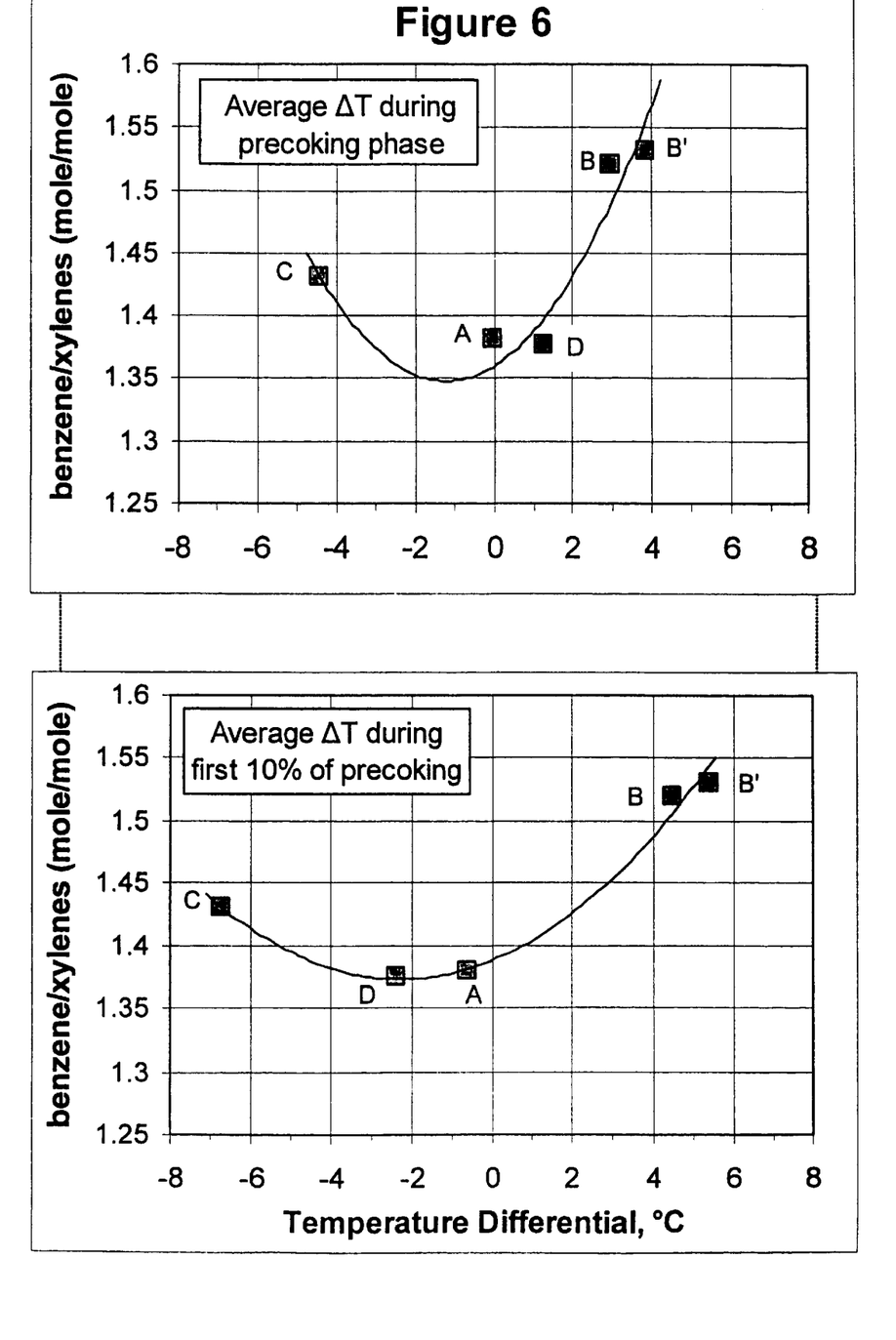
FIG. 6 compares selectivity of various tests as benzene/xylenes ratio as a function of the temperature differential across catalyst beds.

The benefit of the invention is further illustrated in FIG. 6, which is a plot of benzene/xylenes for the above cases normalized to a paraxylene/xylenes ratio of 88%. Data are shown for both the average temperature differential over the total precoking phase and for the first 10% of precoking, when most of the coke is deposited. There is a "volcano effect" of favorable xylenes efficiency when the invention is practiced with little or no temperature differential across the catalyst bed per Tests A and D, i.e., this is a critical parameter in determining the approach to precoking/selectivating the catalyst for the disproportionation step.

What is claimed is:

1. A process for the production of paraxylene comprising the steps of:
   (a) selectively precoking a zeolitic catalyst in a catalyst bed by contacting the catalyst with a coke-forming feed at precoking conditions comprising an inlet temperature of from about 300° to about 700° C. and a temperature differential across the bed of the catalyst of between a 3° C. increase and a 4° C. decrease to deposit between about 5 and 40 mass-% carbon on the catalyst and obtain a selectively precoked catalyst; and,
   (b) disproportionating an aromatics-rich feedstock comprising contacting the feedstock with the selectively precoked catalyst bed in a disproportionation zone at disproportionation conditions to obtain a paraxylene-rich product containing paraxylene in excess of its equilibrium concentration at disproportionation conditions.

2. The process of claim 1 wherein the precoking conditions comprise a pressure of from about 100 kPa to 4 MPa absolute, and a liquid hourly space velocity of from about 0.2 to 10 hr$^{-1}$.

3. The process of claim 2 wherein free hydrogen is present in the precoking step (a) in a molar ratio to coke-forming feed of about 0.2 to 5.

4. The process of claim 1 wherein the temperature differential across the bed of catalyst during selective precoking is between about a 2° C. increase and a 4° C. decrease.

5. The process of claim 1 wherein the disproportionation conditions comprise an inlet temperature of from about 200° to about 600° C., a pressure of from about 100 kPa to 6 MPa absolute, and a liquid hourly space velocity of from about 0.2 to 10 hr$^{-1}$.

6. The process of claim 5 wherein free hydrogen is present in the disproportionation zone in a molar ratio to feedstock hydrocarbons of about 0.5 to 10.

7. The process of claim 1 wherein the precoking conditions comprise an inlet temperature at least 50° C. higher than utilized in the disproportionation zone.

8. The process of claim 1 wherein the precoking conditions comprise a pressure at least 100 kPa lower than utilized in the disproportionation zone.

9. The process of claim 1 wherein the precoking conditions comprise a pressure no more than about half of that used in the disproportionation zone.

10. The process of claim 6 wherein the precoking conditions comprise a molar ratio of free hydrogen to feedstock hydrocarbons no more than about half of that utilized in the subsequent disproportionation zone.

11. The process of claim 1 wherein the catalyst comprises oil-dropped spherical catalyst particles.

12. The process of claim 1 wherein the catalyst comprises a zeolitic aluminosilicate having a pore diameter of from about 5 to 8 Å and a refractory inorganic-oxide binder.

13. The process of claim 1 wherein the zeolitic aluminosilicate comprises a pentasil zeolite selected from the group consisting of MFI, MEL, MTW and TON.

14. The process of claim 12 wherein the binder comprises an amorphous aluminum phosphate.

15. The process of claim 1 wherein the aromatics-rich feedstock comprises a toluene-containing feedstock.

16. The process of claim 12 wherein the coke-forming feed comprises a toluene-containing feedstock.

17. The process of claim 8 wherein the proportion of paraxylene to total xylenes is at least based on the total xylenes 80 mass-%.

18. A process for the production of paraxylene comprising the steps of:

(a) selectively precoking a zeolitic catalyst in a catalyst bed by contacting the catalyst with a coke-forming feed at precoking conditions comprising an inlet temperature of from about 300° to about 700° C., a pressure of from about 100 kPa to 4 MPa absolute, a liquid hourly space velocity of from about 0.2 to 10 $hr^{-1}$, a molar ratio of free hydrogen to feedstock hydrocarbons of about 0.2 to 5 and a temperature differential across the bed of the catalyst of between a 3° C. increase and a 4° C. decrease to deposit between about 5 and 40 mass-% carbon on the catalyst and obtain a selectively precoked catalyst; and, (b) disproportionating an aromatics-rich feedstock comprising contacting the feedstock with the selectively precoked catalyst bed in a disproportionation zone at disproportionation conditions comprising an inlet temperature of from about 200° to about 600° C., a pressure of from about 100 kPa to 6 MPa absolute, a liquid hourly space velocity of from about 0.2 to 10 $hr^{-1}$ and a ratio of free hydrogen to feedstock hydrocarbons of about 0.5 to 10 to obtain a paraxylene-rich product containing paraxylene in excess of its equilibrium concentration at disproportionation conditions.

19. A process for the production of paraxylene comprising the steps of:

(a) selectively precoking a zeolitic catalyst in a catalyst bed by contacting the catalyst with a coke-forming feed at precoking conditions comprising an inlet temperature of from about 300° to about 700° C., a pressure of from about 100 kPa to 4 MPa absolute, a liquid hourly space velocity of from about 0.2 to 10 $hr^{-1}$, a molar ratio of free hydrogen to feedstock hydrocarbons of about 0.2 to 5 and a temperature differential across the bed of the catalyst of between a 3° C. increase and a 4° C. decrease to deposit between about 5 and 40 mass-% carbon on the catalyst and obtain a selectively precoked catalyst; and, (b) disproportionating an aromatics-rich feedstock comprising contacting the feedstock with the selectively precoked catalyst bed in a disproportionation zone at disproportionation conditions comprising an inlet temperature of from about 200° to about 600° C., a pressure of from about 100 kPa to 6 MPa absolute, a liquid hourly space velocity of from about 0.2 to 10 $hr^{-1}$ and a ratio of free hydrogen to feedstock hydrocarbons of about 0.5 to 10 to obtain a paraxylene-rich product containing paraxylene in excess of its equilibrium concentration at disproportionation conditions; and, (c) recovering pure paraxylene from the paraxylene-rich product by one or both of adsorption and crystallization.

* * * * *